US011779615B2

(12) United States Patent
Huang et al.

(10) Patent No.: US 11,779,615 B2
(45) Date of Patent: Oct. 10, 2023

(54) LACTIC ACID BACTERIA COMPOSITION FOR REDUCING FAT AND PROMOTING EXERCISE PERFORMANCE AND USE THEREOF

(71) Applicant: GLAC BIOTECH CO., LTD, Tainan (TW)

(72) Inventors: Chi-Chang Huang, Tainan (TW); Mon-Chien Lee, Tainan (TW); Yi-Ju Hsu, Tainan (TW); Hsieh-Hsun Ho, Tainan (TW); Yi-Wei Kuo, Tainan (TW); Wen-Yang Lin, Tainan (TW); Jia-Hung Lin, Tainan (TW); Chi-Huei Lin, Tainan (TW)

(73) Assignee: GLAC BIOTECH CO., LTD, Tainan (TW)

( * ) Notice: Subject to any disclaimer, the term of this patent is extended or adjusted under 35 U.S.C. 154(b) by 14 days.

(21) Appl. No.: 17/378,955

(22) Filed: Jul. 19, 2021

(65) Prior Publication Data
US 2022/0347238 A1 Nov. 3, 2022

(30) Foreign Application Priority Data

Apr. 28, 2021 (CN) .......................... 202110467618.9

(51) Int. Cl.
| | | |
|---|---|---|
| A61K 35/747 | (2015.01) | |
| A61P 3/04 | (2006.01) | |
| C12N 1/20 | (2006.01) | |
| A23L 33/135 | (2016.01) | |
| A61K 35/745 | (2015.01) | |

(52) U.S. Cl.
CPC .......... *A61K 35/747* (2013.01); *A23L 33/135* (2016.08); *A61K 35/745* (2013.01); *A61P 3/04* (2018.01); *C12N 1/205* (2021.05)

(58) Field of Classification Search
CPC combination set(s) only.
See application file for complete search history.

(56) References Cited

FOREIGN PATENT DOCUMENTS

| WO | WO 2017/059101 | * | 4/2017 | |
| WO | WO-2017059101 A1 | * | 4/2017 | ........... A23L 33/105 |

OTHER PUBLICATIONS

Bringel, Françoise (2005). *Lactobacillus plantarum* subsp. *argentoratensis* subsp. nov., isolated from vegetable matrices. International journal of systematic and evolutionary microbiology. 55. 1629-34. 10.1099/ijs.0.63333-0.), (Year: 2005).*

Fatih Ozogul, Imen Hamed. Lactic Acid Bacteria: *Lactobacillus* spp.: *Lactobacillus acidophilus*, Reference Module in Food Science, Elsevier, 2016, ISBN 9780081005965, https://doi.org/10.1016/B978-0-08-100596-5.00852-0.), (Year: 2016).*

(Continued)

*Primary Examiner* — Erin M. Bowers
(74) *Attorney, Agent, or Firm* — Locke Lord LLP; Tim Tingkang Xia, Esq.

(57) ABSTRACT

The present invention provides a lactic acid bacteria composition, which comprises: a *Lactobacillus plantarum* PL-02 strain, a *Lactobacillus acidophilus* TYCA06 strain, a *Lactobacillus casei* CS-773 strain, and a physiologically acceptable excipient, diluent, or carrier. All of the strains are deposited at the China General Microbiological Culture Collection Center.

9 Claims, 11 Drawing Sheets

(56) References Cited

OTHER PUBLICATIONS

Dellaglio, Franco & Dicks, Leon & Du Toit, Maret & Torriani, Sandra. (1991). Designation of ATCC 334 in Place of ATCC 393 (NCDO 161) as the Neotype Strain of Lactobacillus casei (Collins et al., 1989) International Journal of Systematic Bacteriology. 41. 10.1099/00207713-41-2-340 (Year: 1991).*
Reuter, G. (1971). Designation of Type Strains for *Bifidobacterium* Species. International Journal of Systematic and Evolutionary Microbiology, 21, 273-275.), (Year: 1971).*
Matthew D. Collins, Brian A. Phillips, Paolo Zanoni. (1989). Deoxyribonucleic Acid Homology Studies of Lactobacillus casei, International Journal of Systematic and Evolutionary Microbiology, https://doi.org/10.1099/00207713-39-2-105 (Year: 1989).*
Nomura M, Kobayashi M, Narita T, Kimoto-Nira H, Okamoto T. Phenotypic and molecular characterization of Lactococcus lactis from milk and plants. J Appl Microbiol. Aug. 2006;101(2):396-405. doi: 10.1111/j.1365-2672.2006.02949.x. PMID: 16882147.) (Year: 2006).*

* cited by examiner

LACTIC ACID BACTERIA COMPOSITION FOR REDUCING FAT AND PROMOTING EXERCISE PERFORMANCE AND USE THEREOF

CROSS REFERENCE

This non-provisional application claims priority of China Invention Patent Application No. 202110467618.9, filed on Apr. 28, 2021, the contents thereof are incorporated by reference herein.

FIELD OF THE INVENTION

The present invention is directed to a composition, and particularly to a lactic acid bacteria composition for reducing fat and promoting exercise performance. The present invention also covers the use of the foregoing lactic acid bacteria composition.

BACKGROUND OF THE INVENTION

Obesity is a global modern lifestyle disease, and the World Health Organization (WHO) warns that obesity is a chronic disease. According to the announcement of ten leading death causes in Taiwan in 2017, seven causes are related to obesity. Obesity occurs due to excessive calorie intake and less calorie consumption so as to convert calorie to fat and accumulate fat in the body. In addition to inheritance, environment and lifestyle are the causes for obesity. In clinical nutriology, the body mass index (BMI) or the waistline is used as an assessment indicator for obesity. In Taiwan, overweight occurs with 24≤BMI<27, slight obesity occurs with 27≤BMI<30, middle obesity occurs with 30≤BMI<35, and extreme obesity occurs with BMI≥35. It has been reported that diabetes, cardiovascular disease, metabolic syndrome, gallbladder disease, dyslipidemia, dyspnea, sleep apnoea, and cancer have a certain degree of relevance to overweight or obesity. It also has been reported that the decrease of body weight by more than 5%, e.g., the decrease of body weight of 90 kg by 5 kg, is beneficial to the health so as to ameliorate hypertension or diabetes. It further has been reported that improperly dieting for weight loss often reduces human's muscle, not fat, which has bad effects on human's health. Muscle is mainly responsible for body's basal metabolism, and muscle reduction can result in exhaustion and poor balance to increase the risk of fall and fracture.

When the human or the animal is fed with probiotics, the quality of gastrointestinal microflora can be improved to promote digestion and health.

Accordingly, probiotics are safe to human's body; however, probiotics must live in the host's body to improve his/her health. As above, there is a need to find a lactic acid bacterial strain which has effects on promoting weight loss, reducing body fat and blood fat, and enhancing muscle strength and endurance. Then, a safe supplement which is able to be taken chronically is developed by adding the lactic acid bacterial strain.

SUMMARY OF THE INVENTION

The present invention is made based on the discovery that a lactic acid bacteria composition has effects on decreasing body weight and reducing body fat and blood fat. It is further discovered that the foregoing composition can provide mice with a better performance on forelimb grip strength and running endurance than the commercial product *Lactobacillus plantarum* TWK10 strain can.

An objective of the present invention is to provide a lactic acid bacteria composition which can decrease body weight, promote exercise performance, and enhance body composition to have effects on enhancing muscle strength and muscle endurance.

Therefore, the present invention provides a lactic acid bacteria composition, the composition comprises: a *Lactobacillus plantarum* PL-02 strain (accession number: CGMCC 20485), a *Lactobacillus acidophilus* TYCA06 strain (accession number: CGMCC 15210), a *Lactobacillus casei* CS-773 strain (accession number: CGMCC 20991), and a physiologically acceptable excipient, diluent, or carrier, and all of the strains are deposited at the China General Microbiological Culture Collection Center.

Preferably, the composition additionally comprises: a *Bifidobacterium longum* subsp. *infantis* BLI-02 strain (accession number: CGMCC 15212) and a *Lactobacillus rhamnosus* bv-77 strain (accession number: CCTCC M 2014589), the *Bifidobacterium longum* subsp. *infantis* BLI-02 strain is deposited at the China General Microbiological Culture Collection Center, and the *Lactobacillus rhamnosus* bv-77 strain is deposited at the China Center for Type Culture Collection.

Preferably, the composition further comprises: a *Bifidobacterium longum* subsp. *infantis* BLI-02 strain (accession number: CGMCC 15212) and a *Lactococcus lactis* LY-66 strain (accession number: CGMCC 21838), and both of the strains are deposited at the China General Microbiological Culture Collection Center.

Preferably, the composition is a food composition or a pharmaceutical composition.

Preferably, the physiologically acceptable excipient, diluent, or carrier is a food, the food is milk product, tea, coffee, candy, or energy drink, and the milk product is fermented milk, yogurt, cheese, or milk powder.

Preferably, the pharmaceutical composition is in an oral dosage form, and the oral dosage form is a tablet form, a capsule form, a solution form, or a powder form.

Preferably, total bacterial count of the composition is more than $10^6$ CFU.

The present invention also provides a method for reducing fat and promoting exercise performance by administering the composition to a subject in need thereof.

DETAILED DESCRIPTION OF THE INVENTION

The detailed description and preferred embodiments of the invention will be set forth in the following content, and provided for people skilled in the art to understand the characteristics of the invention.

The freeze-dried culture of each lactic acid bacterial strain according to the present invention is deposited at the China Center for Type Culture Collection in Wuhan University, Wuhan City, China or deposited at the China General Microbiological Culture Collection Center in No. 3, No. 1 Courtyard, Beichen West Road, Chaoyang District, Beijing City, China. The deposition information is listed in Table 1 below.

TABLE 1

Deposition information of lactic acid bacterial strains

| Strain | Classification | Accession number | Deposition date |
|---|---|---|---|
| PL-02 | Lactobacillus plantarum | CGMCC 20485 | Aug. 6, 2020 |
| TYCA06 | Lactobacillus acidophilus | CGMCC 15210 | Jan. 15, 2018 |
| CS-773 | Lactobacillus casei | CGMCC 20991 | Nov. 2, 2020 |
| BLI-02 | Bifidobacterium longum subsp. infantis | CGMCC 15212 | Jan. 15, 2018 |
| bv-77 | Lactobacillus rhamnosus | CCTCC M 2014589 | Nov. 24, 2014 |
| LY-66 | Lactococcus lactis | CGMCC 21838 | Feb. 26, 2021 |

It is discovered that a PL-02 strain, a TYCA06 strain, and a CS-773 strain have effects on reducing body weight, promoting exercise performance, and reducing body fatigue, a BLI-02 strain and a bv-77 strain have effects on reducing body weight, and a BLI-02 strain and a LY-66 strain have effects on promoting exercise performance.

In an embodiment, a composition for reducing fat and promoting exercise performance according to the present invention includes: (a) isolated bacterial strains, the isolated strains comprising: a Lactobacillus plantarum PL-02 strain (accession number: CGMCC 20485), a Lactobacillus acidophilus TYCA06 strain (accession number: CGMCC 15210), and a Lactobacillus casei CS-773 strain (accession number: CGMCC 20991); and (b) a physiologically acceptable excipient, diluent, or carrier.

In order to additionally enhance the effect on body weight reduction, the isolated bacterial strains further comprise: a Bifidobacterium longum subsp. infantis BLI-02 strain (accession number: CGMCC 15212) and a Lactobacillus rhamnosus bv-77 strain (accession number: CCTCC M 2014589).

In order to additionally enhance the effect on exercise performance promotion, the isolated bacterial strains further comprise: a Bifidobacterium longum subsp. infantis BLI-02 strain (accession number: CGMCC 15212) and a Lactococcus lactis LY-66 strain (accession number: CGMCC 21838).

Preferably, the physiologically acceptable excipient, diluent, or carrier is a pharmaceutically acceptable excipient, diluent, or carrier so that the composition can be used as a pharmaceutical composition.

Preferably, the physiologically acceptable excipient, diluent, or carrier is an edibly acceptable excipient, diluent, or carrier so that the composition can be used as a food composition.

On the condition that the composition is a pharmaceutical composition, the composition is in an oral dosage form, e.g., a tablet form, a capsule form, a solution form, or a powder form.

On the condition that the composition is a food composition, the physiologically acceptable excipient, diluent, or carrier may be a food. The food is exemplarily milk product, tea, coffee, candy, or energy drink, and the milk product is exemplarily fermented milk, yogurt, cheese, or milk powder.

Preferably, the isolated bacterial strains are individually a viable strain or an inactivated strain. Further, on the condition that the composition is a pharmaceutical composition or a food composition, total bacterial count of the composition is more than $10^6$ CFU, and preferably is more than $10^{10}$ CFU.

EXAMPLE 1

Morphological and Common Properties of Bacterial Strains

The 16S ribosomal RNA (rRNA) sequencing and the API bacterial identification system were used to identify the morphological properties of bacterial strains. The morphological properties and common properties of bacterial strains used in this example are listed in Table 2 below.

TABLE 2

Morphological and common properties of lactic acid bacterial strains

| Strains | Properties |
|---|---|
| Lactobacillus plantarum PL-02 strain | (1) They are facultative anaerobes, and able to live in low or normal oxygen concentration.<br>(2) The suitable temperature for survival is 10-45° C., and the most suitable temperature is 30-35° C. However, they can still survive at the temperature close to the freezing point.<br>(3) The most suitable pH for growth ranges from pH 3.5 to 4.2, and the most suitable salinity tolerance for growth is 13%-15%.<br>(4) They are in the shape of a linear-rod, and two ends thereof are in the form of a circle. They have a width of 0.9-1.2 mm and a length of 3.0-8.0 mm, and appear alone, appear in pairs, or arrange in short chains. |

TABLE 2-continued

Morphological and common properties of lactic acid bacterial strains

| Strains | Properties |
| --- | --- |
| *Lactobacillus acidophilus* TYCA06 strain | (1) They grow on a MRS agar medium in the shape of a short rod or a long rod, and two ends thereof are in the form of a square. They usually appear alone, appear in pairs, or arrange in short chains.<br>(2) They are gram-positive and non-sporogenous bacteria without catalase and oxidase and without mobility.<br>(3) They can survive in an aerobic environment or an anaerobic environment, and the most suitable temperature for survival is 37 ± 1° C. They are facultative fermentative bacteria and can't produce any gas during glucose metabolism. |
| *Lactobacillus casei* CS-773 strain | (1) They are pleomorphic bacteria which may be in the shape of a short rod or a long rod, have various lengths, and generally have a width of less than 1.5 μm.<br>(2) Their two ends are flush with each other and in the shape of a square, and they often arrange in short chains or long chains; sometimes, they are in the shape of a ball.<br>(3) They are gram-positive and non-sporogenous bacteria without mobility. |
| *Bifidobacterium longum* subsp. *infantis* BLI-02 strain | (1) They grow on a MRS agar medium in the shape of a short rod, and two ends thereof are in the form of an ellipse. They usually appear alone, appear in pairs, or arrange in short chains.<br>(2) They are gram-positive and non-sporogenous bacteria without catalase and oxidase and without mobility.<br>(3) They can survive in an aerobic environment or an anaerobic environment, and the most suitable temperature for survival is 37 ± 1° C. They are facultative heterofermentative bacteria and can't produce any gas during glucose metabolism. |
| *Lactobacillus rhamnosus* bv-77 strain | (1) They grow on a MRS agar medium in an irregular shape, i.e., a Y shape, a V shape, or a curve shape, they are in small size, and usually appear alone.<br>(2) They are gram-positive and non-sporogenous bacteria without catalase and oxidase and without mobility.<br>(3) They can survive in an absolutely anaerobic environment, and the most suitable temperature for survival is 37 ± 1° C. They are facultative heterofermentative bacteria and can't produce any gas during glucose metabolism. |
| *Lactococcus lactis* LY-66 strain | (1) They are gram-positive bacteria and are widely used for the production of buttermilk or cheese.<br>(2) They appear in pairs or arrange in short chains; according to the growth condition, their oval shape typically has a length of 0.5-1.5 μm.<br>(3) They are non-sporogenous bacteria without mobility. They are homofermentative bacteria which can convert sugar to L-(+)-lactic acid.<br>(4) They are aerobic bacteria, and can be cultured in a M17 medium at 37 ± 1° C. |

EXAMPLE 2

Cultivation and Administration of Bacterial Strains

Strains were stored in 20% glycerol at -80° C. Before used, strains were activated using a MRS medium (DIFCO) containing 0.05% cysteine at 37° C. for 24 hours twice. The daily dose of strain administration to a 60-kg human was $2 \times 10^{10}$ CFU/day. That was, the suggested daily dose of strain administration per kg of human's body weight was $3.33 \times 10^{8}$ CFU/kg/day. In view of "Estimating the Maximum Safe Starting Dose in Initial Clinical Trials for Therapeutics in Adult Healthy Volunteers" established by the U.S. Food and Drug Administration (FDA) in 2005, the factor from human dose to mouse dose was 12.3; therefore, it was learnt that the daily dose of strain administration per kg of mouse' body weight was $4.1 \times 10^{9}$ CFU/kg/day. Mice used in this example weighed 30 g; therefore, the daily dose of strain administration to each mouse was $1.23 \times 10^{8}$ CFU/day. In this example, administration was performed at 9 a.m. every day. Generally, the strain concentration was adjusted to $4.1 \times 10^{8}$ CFU/mL with PBS, and then 0.3 mL of PBS containing the strain(s) was administered to each mouse. In another aspect, 0.3 mL of pure PBS was administered to each reference mouse.

EXAMPLE 3

Measurement of Body Weight and Body Fat Weight

In this example, the following parameters were detected after administration to mice in consecutive 10 weeks: (1) body weight; and (2) body fat weight. Generally, the body weight was obtained by weighing the mice periodically, and then the body weight at the start of test was compared with that at the end of test. At the end of test, each mouse was sacrificed to collect its fat tissues surrounding the kidney, the mesentery, and the testis and then the fat tissues were weighed.

Figure 1:
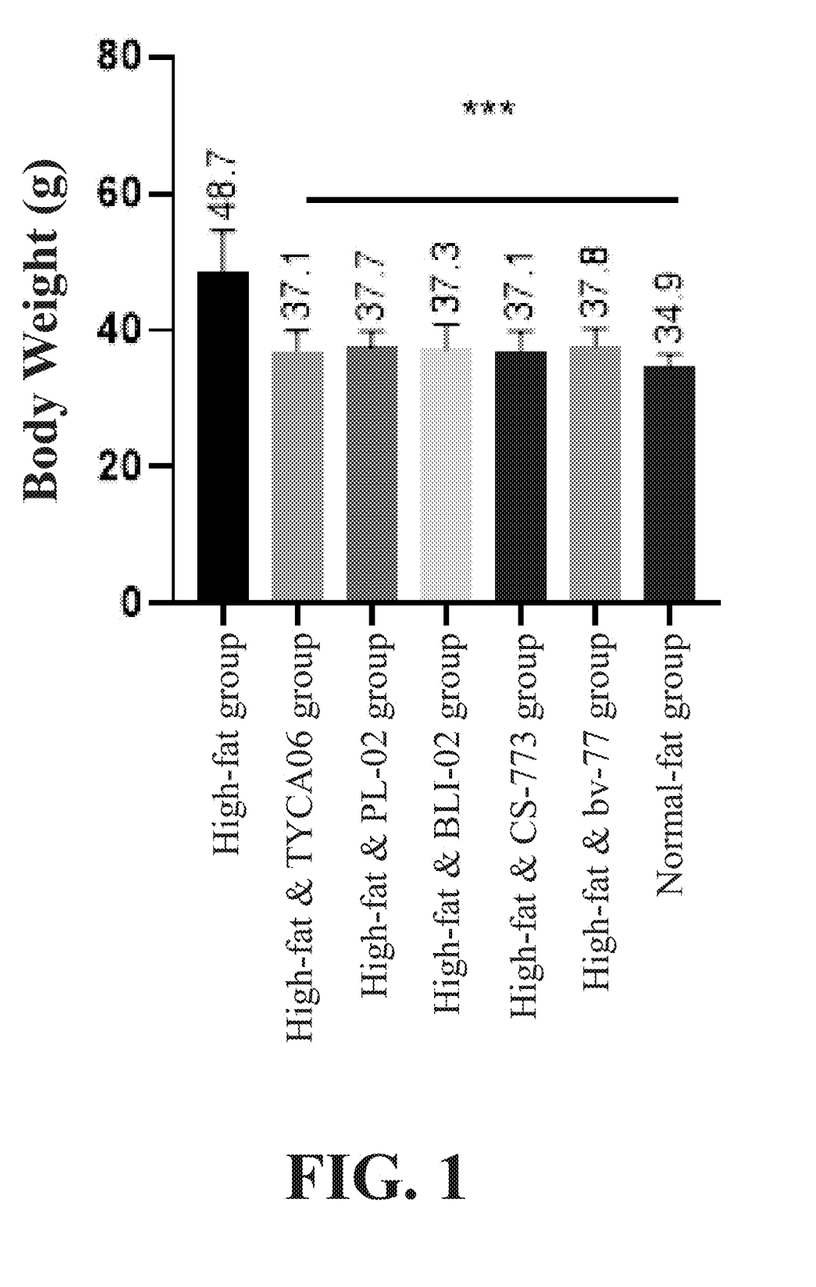
FIG. 1 is a bar graph illustrating the body weight of mice after administration of various diets in consecutive 10 weeks.

FIG. 1 presents the mice's body weight after 10-week consecutive administration of various diets. The body weight after administration of the high-fat diet (high-fat group) is higher than that after administration of the normal-fat diet (normal-fat group) (high-fat group: 48.7±5.9 g; normal-fat group: 34.9±1.6 g). Relative to the body weight after administration of the high-fat diet (high-fat group), the body weight after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), that after administration of the high-fat diet and the probiotics CS-773 strain (high-fat & CS-773 group), and that after administration of the high-fat diet and the probiotics bv-77 strain (high-fat & bv-77 group) all are reduced by approximately 11 g. These results demonstrate that taking TYCA06 strain, PL-02 strain, BLI-02 strain, CS-773 strain, or bv-77 strain can alleviate the body weight gain caused by a high-fat diet.

Figure 2:
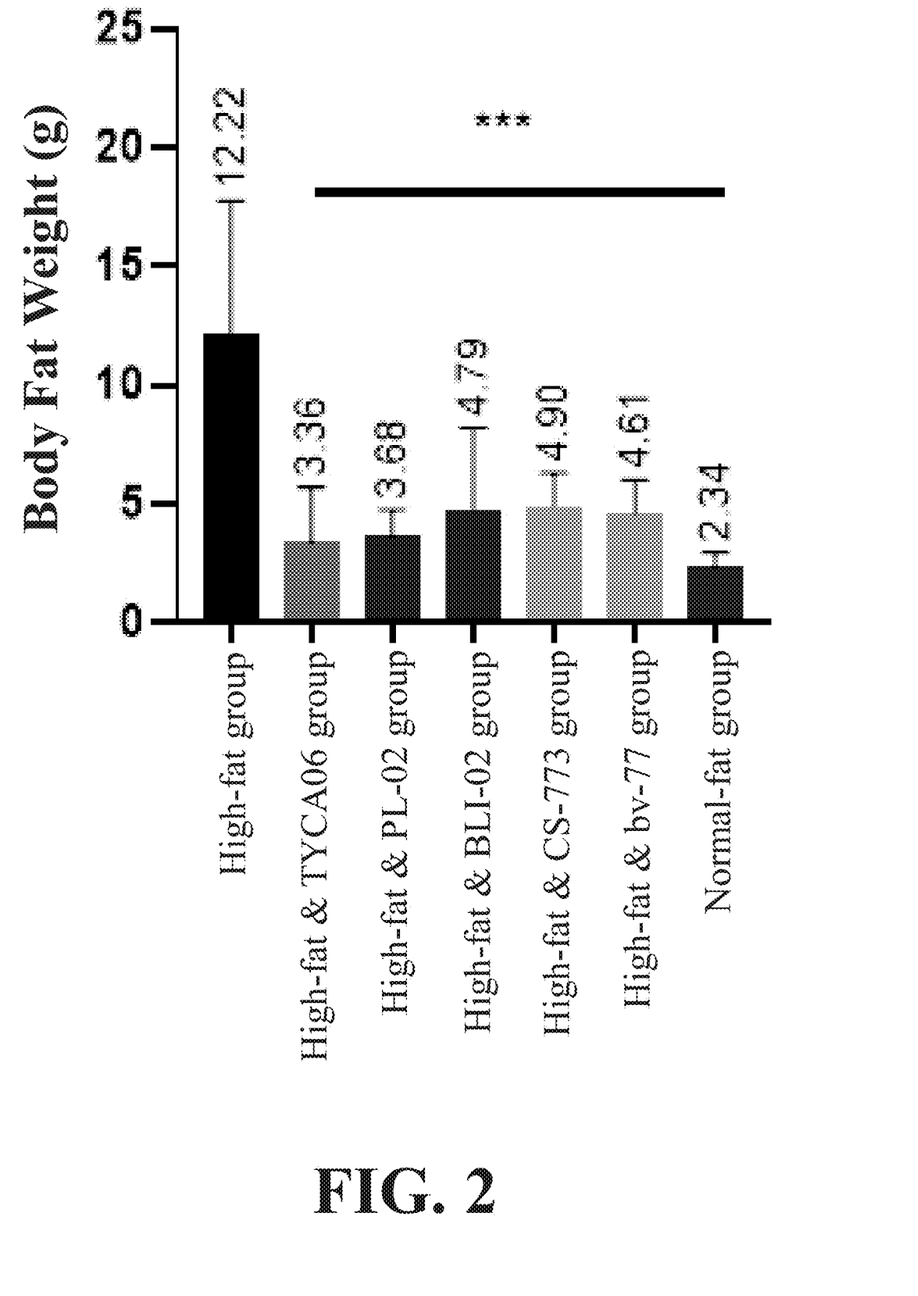
FIG. 2 is a bar graph illustrating the body fat weight of mice after administration of various diets in consecutive 10 weeks.

FIG. 2 presents the mice's body fat weight after 10-week consecutive administration of various diets. In light of "Method for Assessing Function of Health Food to Reduce Body Fat," total weight of fat tissues surrounding the kidney, the mesentery, and the testis is defined as body fat weight. Relative to the body fat weight after administration of the normal-fat diet (normal-fat group), the body fat weight after administration of the high-fat diet (high-fat group) is obviously increased (high-fat group: 12.22±5.57 g; normal-fat group: 2.34±0.61 g). As compared to the body fat weight after administration of the high-fat diet (high-fat group), the body fat weight after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), that after administration of the high-fat diet and the probiotics CS-773 strain (high-fat & CS-773 group), and that after administration of the high-fat diet and the probiotics bv-77 strain (high-fat & bv-77 group) all are obviously reduced. These results demonstrate that taking TYCA06 strain, PL-02 strain, BLI-02 strain, CS-773 strain, or bv-77 strain can alleviate the body fat weight gain caused by a high-fat diet.

Figure 3:
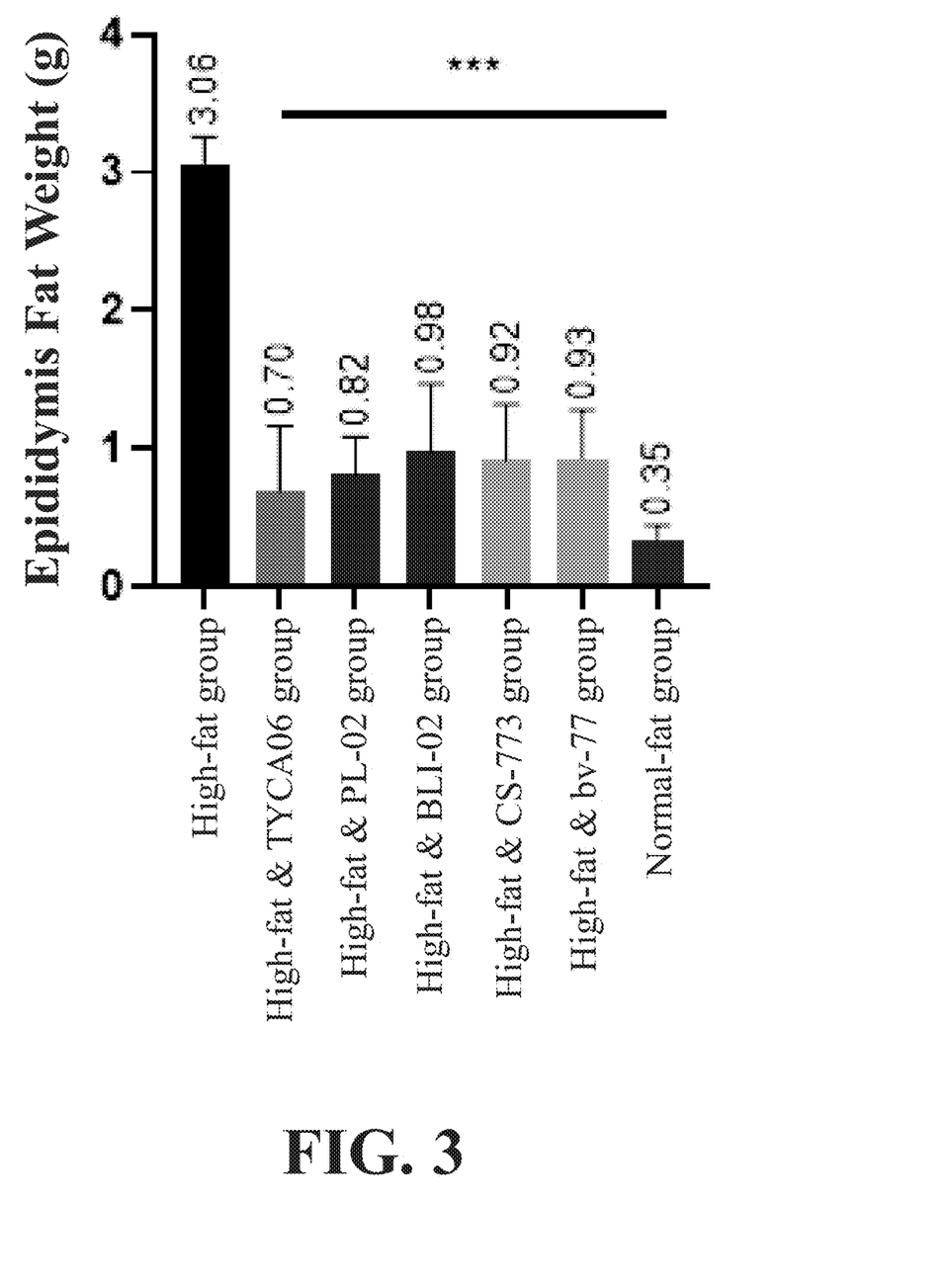
FIG. 3 is a bar graph illustrating the epididymis fat weight of mice after administration of various diets in consecutive 10 weeks.

FIG. 3 presents the mice's epididymis fat weight after 10-week consecutive administration of various diets. The epididymis fat weight after administration of the high-fat diet (high-fat group) is higher than that after administration of the normal-fat diet (normal-fat group) (high-fat group: 3.06±0.2 g; normal-fat group: 0.35±0.1 g). Relative to the epididymis fat weight after administration of the high-fat diet (high-fat group), the epididymis fat weight after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), that after administration of the high-fat diet and the probiotics CS-773 strain (high-fat & CS-773 group), and that after administration of the high-fat diet and the probiotics bv-77 strain (high-fat & bv-77 group) all are reduced. These results demonstrate that taking TYCA06 strain, PL-02 strain, BLI-02 strain, CS-773 strain, or bv-77 strain can alleviate the offal fat weight gain caused by a high-fat diet.

EXAMPLE 4

Aanalysis of Blood Biochemistry

In this example, after administration to mice in consecutive 10 weeks, 2 mL of mouse' blood was collected. After which, the blood total cholesterol content, the blood triglyceride content, and the blood low-density lipoprotein content were measured by a biochemical analyzer.

Figure 4:
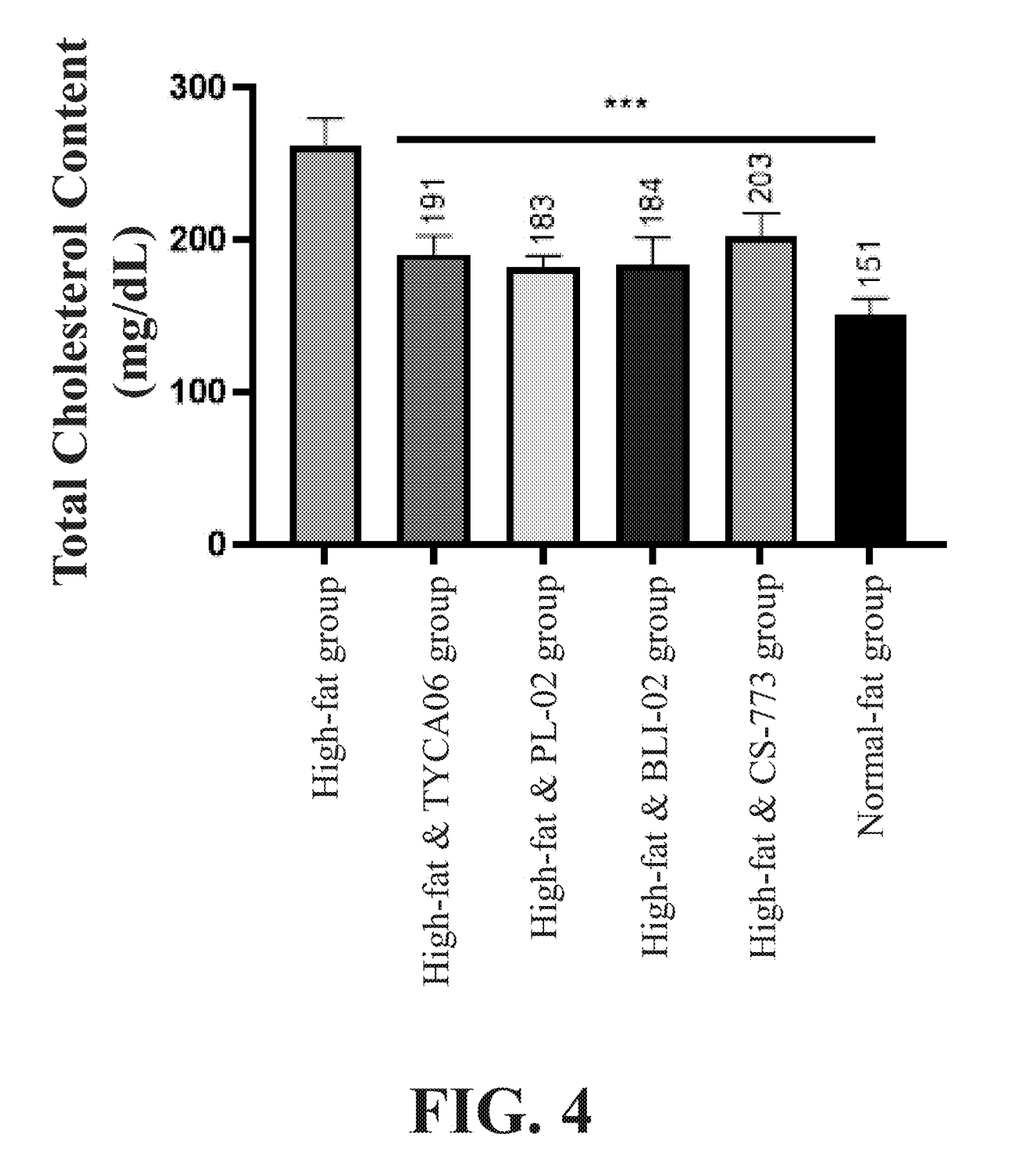
FIG. 4 is a bar graph illustrating the blood total cholesterol (TC) content of mice after administration of various diets in consecutive 10 weeks.

FIG. 4 presents the mice's blood total cholesterol content after 10-week consecutive administration of various diets. The blood total cholesterol content after administration of the high-fat diet (high-fat group) is higher than that after administration of the normal-fat diet (normal-fat group) (high-fat group: 262±18 mg/dL; normal-fat group: 151±11 mg/dL). Relative to the blood total cholesterol content after administration of the high-fat diet (high-fat group), the blood total cholesterol content after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), and that after administration of the high-fat diet and the probiotics CS-773 strain (high-fat & CS-773 group) all are reduced. These results demonstrate that taking TYCA06 strain, PL-02 strain, BLI-02 strain, or CS-773 strain can alleviate the high cholesterol level caused by a high-fat diet.

Figure 5:
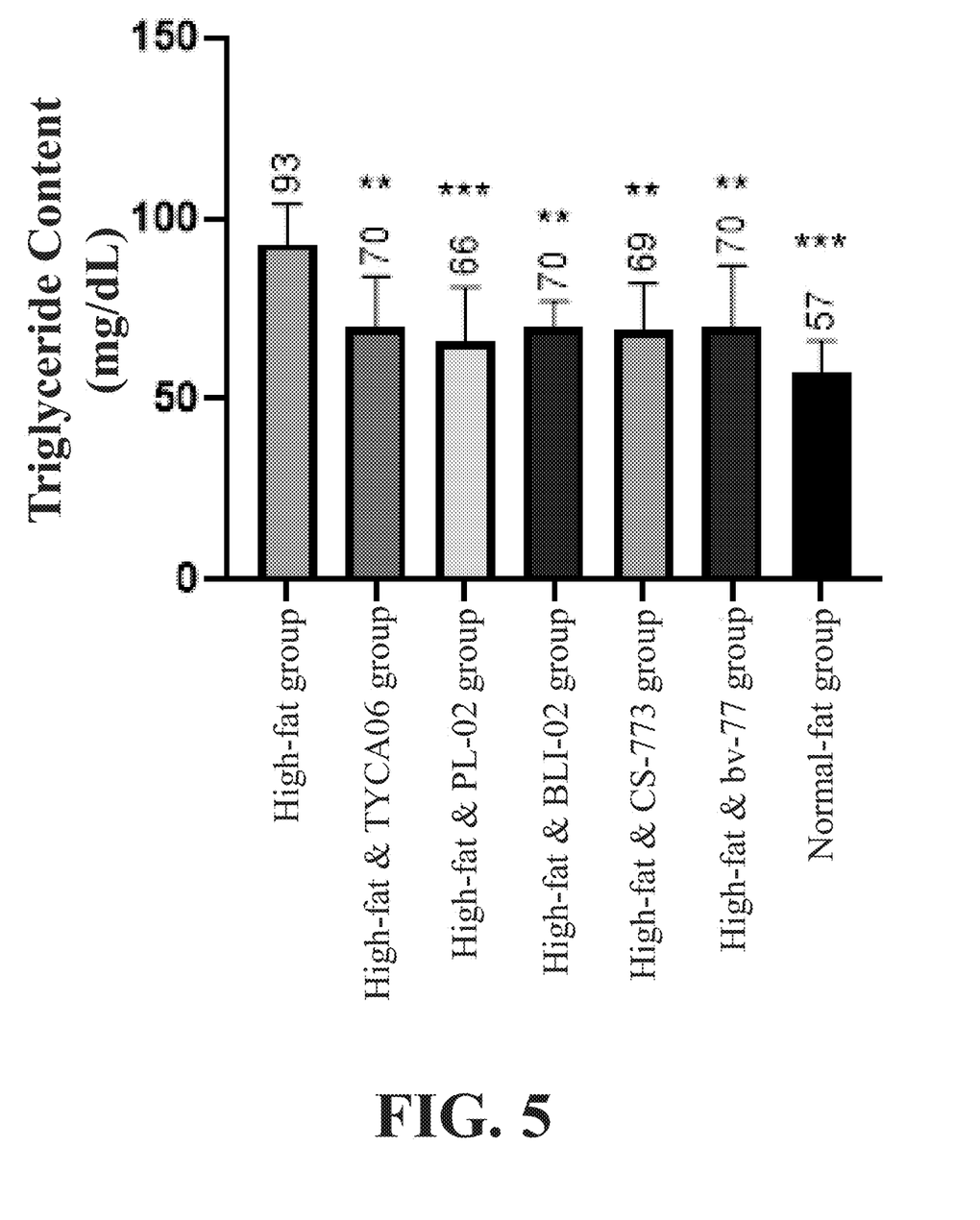
FIG. 5 is a bar graph illustrating the blood triglyceride (TG) content of mice after administration of various diets in consecutive 10 weeks.

FIG. 5 presents the mice's blood triglyceride content after 10-week consecutive administration of various diets. The blood triglyceride content after administration of the high-fat diet (high-fat group) is higher than that after administration of the normal-fat diet (normal-fat group) (high-fat group: 93±11 mg/dL; normal-fat group: 57±9 mg/dL). Relative to the blood triglyceride content after administration of the high-fat diet (high-fat group), the blood triglyceride content after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), that after administration of the high-fat diet and the probiotics CS-773 strain (high-fat & CS-773 group), and that after administration of the high-fat diet and the probiotics bv-77 strain (high-fat & bv-77 group) all are reduced. These results demonstrate that taking TYCA06 strain, PL-02 strain, BLI-02 strain, CS-773 strain, or bv-77 strain can alleviate the high triglyceride level caused by a high-fat diet.

Figure 6:
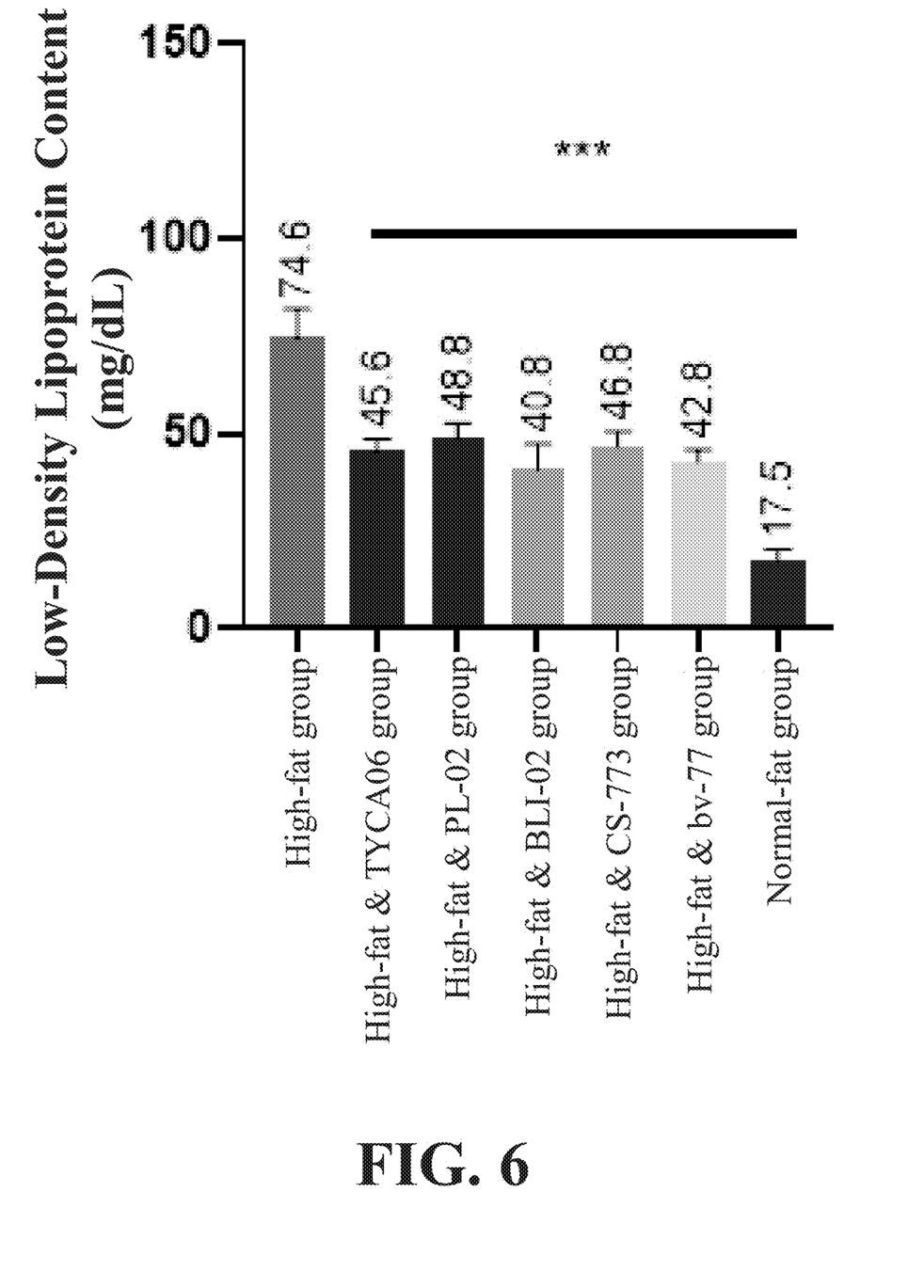
FIG. 6 is a bar graph illustrating the blood low-density lipoprotein (LDL) content of mice after administration of various diets in consecutive 10 weeks.

FIG. 6 presents the mice's blood low-density lipoprotein content after 10-week consecutive administration of various diets. The blood low-density lipoprotein content after administration of the high-fat diet (high-fat group) is higher than that after administration of the normal-fat diet (normal-fat group) (high-fat group: 74.6±7.3 mg/dL; normal-fat group: 17.5±2.9 mg/dL). Relative to the blood low-density lipoprotein content after administration of the high-fat diet (high-fat group), the blood low-density lipoprotein content after administration of the high-fat diet and the probiotics TYCA06 strain (high-fat & TYCA06 group), that after administration of the high-fat diet and the probiotics PL-02 strain (high-fat & PL-02 group), that after administration of the high-fat diet and the probiotics BLI-02 strain (high-fat & BLI-02 group), that after administration of the high-fat diet and the probiotics CS-773 strain (high-fat & CS-773 group), and that after administration of the high-fat diet and the probiotics bv-77 strain (high-fat & bv-77 group) all are reduced. In a non-provided figure, the mice's blood low-density lipoprotein content after 10-week consecutive administration of the high-fat diet and the commercial probiotics LGG strain is 54.9±6.6 mg/dL, which is lower than the blood low-density lipoprotein content of the high-fat & TYCA06 group, that of the high-fat & PL-02 group, that of the high-fat & BLI-02 group, that of high-fat & CS-773 group, and that of the high-fat & bv-77 group. These results demonstrate that taking TYCA06 strain, PL-02 strain, BLI-02 strain, CS-773 strain, or bv-77 strain can alleviate the high low-density lipoprotein level caused by a high-fat diet.

EXAMPLE 5

Animal Forelimb Grip Strength Test

Figure 7:
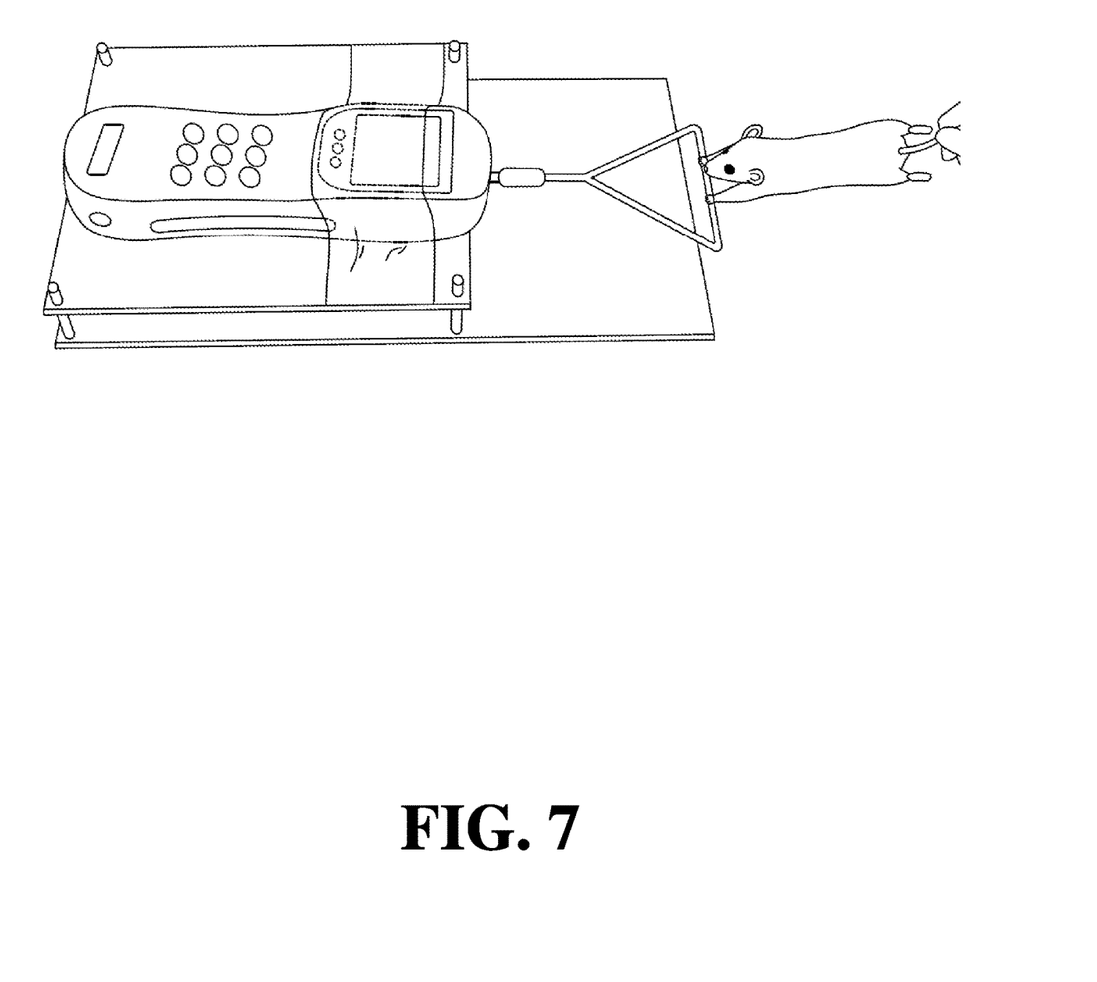
FIG. 7 is a picture showing the mouse forelimb grip strength test.

In this example, after administration to mice in consecutive 4 weeks, forelimb grip strength test was performed for 30 minutes using a grip strength meter to determine the effects of administration on the mice' muscle performance. FIG. 7 shows the forelimb grip strength test, and Nutrients. 2014 Jul. 18; 6(7):2681-96, Molecules. 2013 Apr. 19; 18(4): 4689-702, and Molecules. 2014 Mar 3; 19(3):2793-807 are referred to for the details of the test. Because the animal's body weight interfered with the obtained grip strength, the mice' relative grip strength was used to indicate grip performance. The mice' relative grip strength was calculated according to the following formula:

$$\text{Relative grip strength} = \frac{\text{Grip strength}}{\text{Body Weight}} \times 100\%$$

Figure 8:
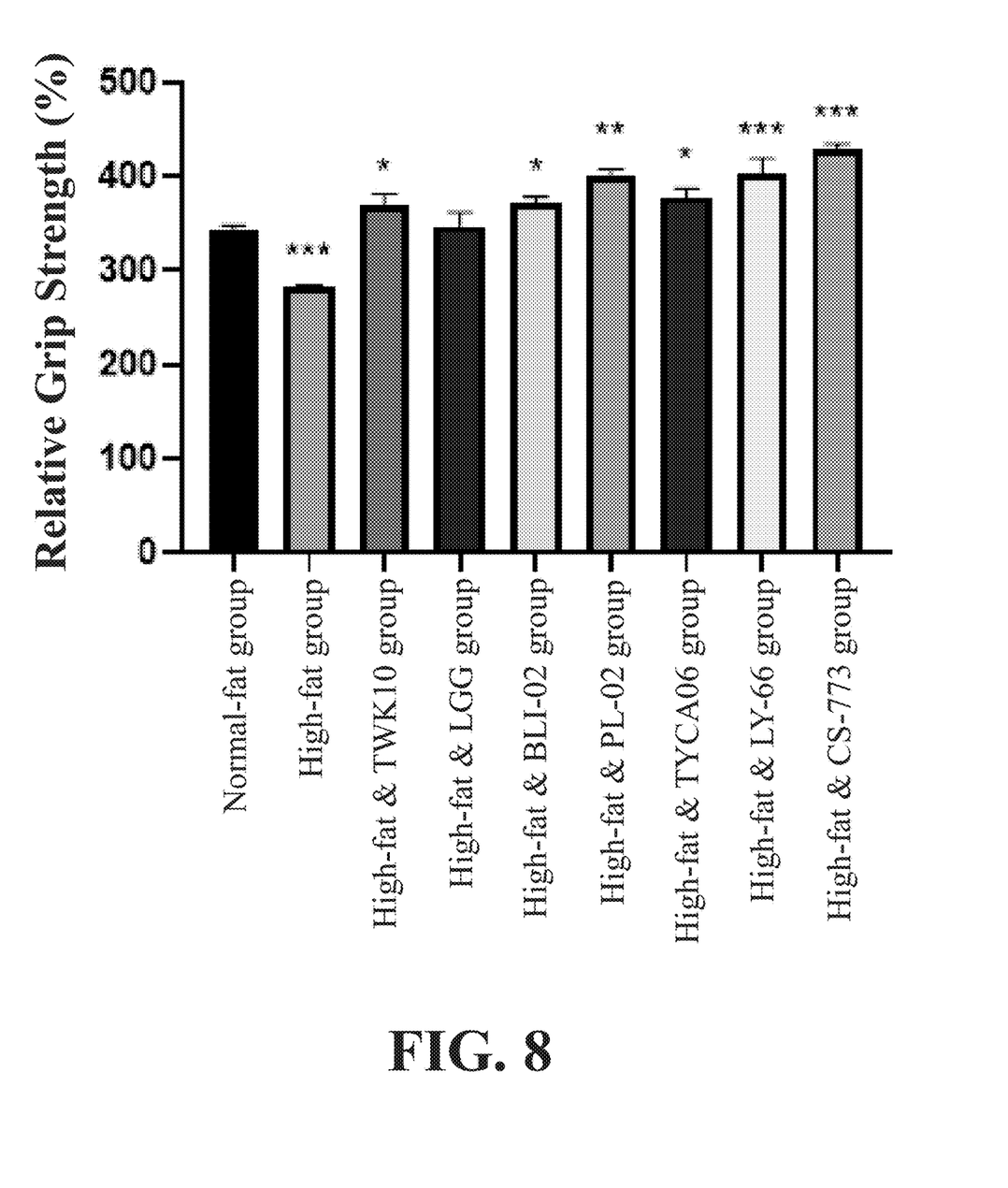
FIG. 8 is a bar graph illustrating the relative grip strength of mice after administration of various diets in consecutive 4 weeks.

FIG. 8 presents the mice's grip performance after 4-week consecutive administration of various diets. The relative grip strength after administration of the normal-fat diet (normal-fat group) is 343±14%; the relative grip strength after administration of the high-fat diet (high-fat group) is 280±8%; the relative grip strength after administration of the high-fat diet and the commercial probiotics TWK10 strain (high-fat & TWK10 group) is 369±34%; the relative grip strength after administration of the high-fat diet and the commercial probiotics LGG strain (high-fat & LGG group) is 346±40%; the relative grip strength after administration of the high-fat diet and the probiotics BLI-02 strain (high-fat & BLI-02 group) is 371±20%; the relative grip strength after administration of the high-fat diet and the probiotics PL-02 strain (high-fat & PL-02 group) is 400±19%; the relative grip strength after administration of the high-fat diet and the probiotics TYCA06 strain (high-fat & TYCA06 group) is 378±24%; the relative grip strength after administration of the high-fat diet and the probiotics LY-66 strain (high-fat & LY-66 group) is 403±43%; the relative grip strength after administration of the high-fat diet and the probiotics CS-773 strain (high-fat & CS-773 group) is 428±17%. These results demonstrate that taking BLI-02 strain, PL-02 strain, TYCA06 strain, LY-66 strain, or CS-773 strain can enhance mice' grip exercise performance.

EXAMPLE 6

Exhaustive Running Test

In this example, after administration to mice in consecutive 4 weeks, the mice' endurance was analyzed. In light of "Method for Assessing Function of Health Food for Anti-Fatigue," the mice were preconditioned for the running test on a treadmill (MK680C, Muromachi Kikai Co. Ltd) at minute 30 after every administration in the last week prior to the test. J Gerontol A Biol Sci Med Sci. 2009 September; 64(9):940-8 is referred to for the test. Generally, the mice ran for 5 minutes at an initial rate of 10 m/min in an incline of 5%. After which, the speed increased by 2 m/min every minute until the mice fell into the shock zone for many times or did not continuously advance in the shock zone, and then the mice were determined to be exhausted.

Figure 9:
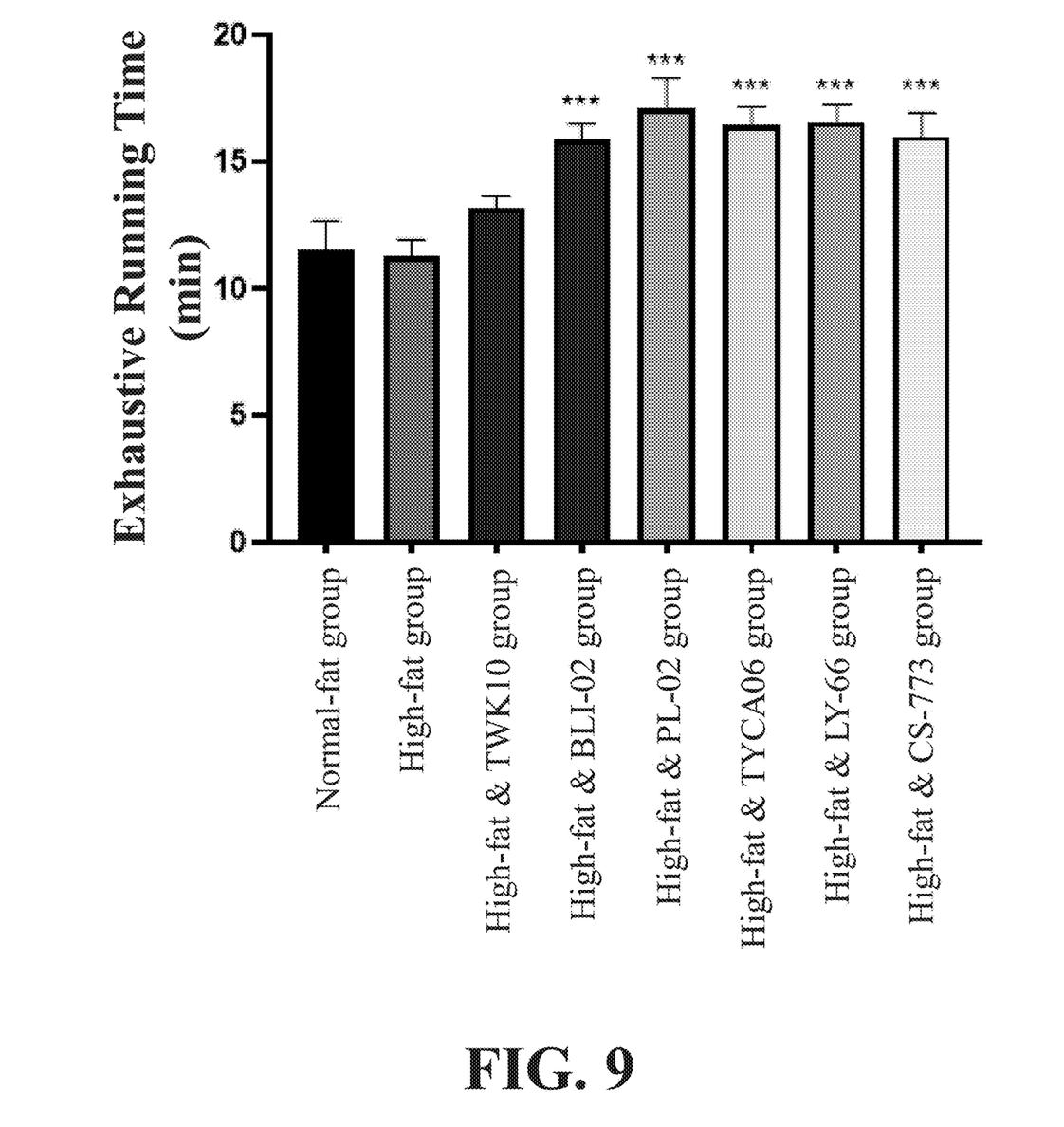
FIG. 9 is a bar graph illustrating the exhaustive running time of mice after administration of various diets in consecutive 4 weeks.

FIG. 9 presents the mice's exhaustive running time after 4-week consecutive administration of various diets. The exhaustive running time after administration of the normal-fat diet (normal-fat group) is 11±3 min; the exhaustive running time after administration of the high-fat diet (high-fat group) is 11±1 min; the exhaustive running time after administration of the high-fat diet and the commercial probiotics TWK10 strain (high-fat & TWK10 group) is 13±1 min; the exhaustive running time after administration of the high-fat diet and the probiotics BLI-02 strain (high-fat & BLI-02 group) is 16±2 min; the exhaustive running time after administration of the high-fat diet and the probiotics PL-02 strain (high-fat & PL-02 group) is 17±3 min; the exhaustive running time after administration of the high-fat diet and the probiotics TYCA06 strain (high-fat & TYCA06 group) is 16±2 min; the exhaustive running time after administration of the high-fat diet and the probiotics LY-66 strain (high-fat & LY-66 group) is 16±1 min; the exhaustive running time after administration of the high-fat diet and the probiotics CS-773 strain (high-fat & CS-773 group) is 16±2 min. These results demonstrate that taking BLI-02 strain, PL-02 strain, TYCA06 strain, LY-66 strain, or CS-773 strain can enhance mice' endurance performance.

EXAMPLE 7

Anti-Oxidation Test in Muscle Cell

The research paper reported that when muscle had anti-oxidation ability, the muscle could help scavenge oxidation factors so that muscle fatigue reduced. In this example, the effect of probiotics on anti-oxidation in muscle cells was analyzed.

Mouse C2C12 myoblasts were seeded onto a culture plate in a cell density of $2 \times 10^6$ cells/well and incubated with a DMEM medium (containing 10% FBS, 1% Penicillin/Streptomycin, and 0.01 mg/mL human transferrin) for 3 days. After which, a fresh DMEM medium (containing 5% FBS) was used for substitution. After probiotics were activated for 18 hours, the strain concentration was adjusted to $2 \times 10^8$ CFU/mL with a DMEM medium (containing 2% BSA and 500 µM oleic acid (OA)). 2 mL of bacterial liquid was added to each well and incubated with the C2C12 myoblasts in an incubator at 37° C. for 12 hours. After removing the culture medium, the lysis buffer (pH7.0; containing 1 mM EDTA and 50 mM potassium phosphate) was added to each well to break open the cells, and then the supernatant was obtained by centrifugation at a rotation rate of 10,000 rpm at 4° C. for 15 minutes. Finally, the supernatant was analyzed to determine the intracellular catalase activity.

Figure 10:
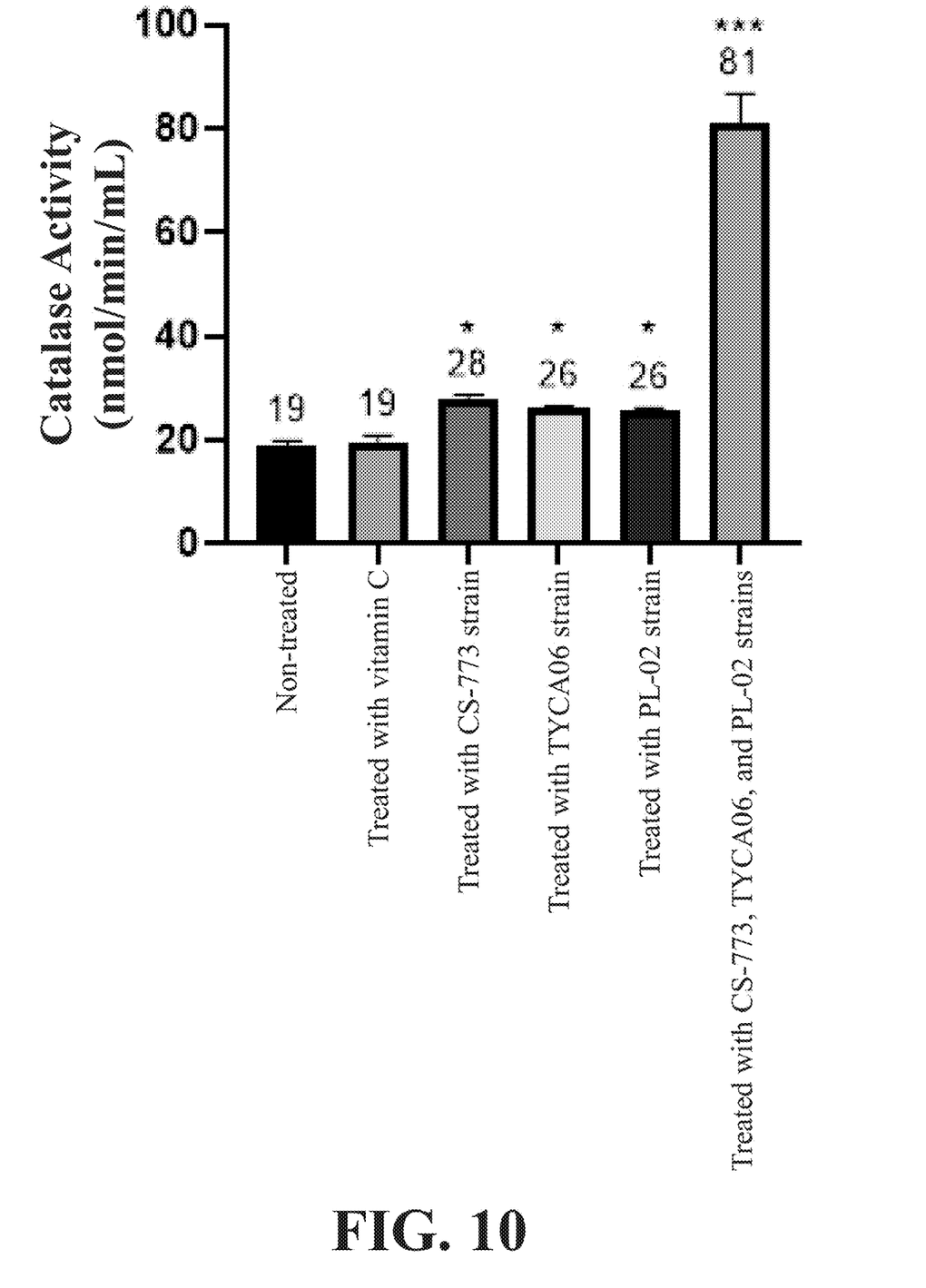
FIG. 10 is a bar graph illustrating the effect of probiotics on anti-oxidation in mouse C2C12 myoblasts.

As shown in FIG. 10, the catalase activity of non-treatment and that of treatment with vitamin C are both 19 nmol/min/mL; the catalase activity of treatment with CS-773 strain is 28 nmol/min/mL; the catalase activity of treatment with TYCA06 strain is 26 nmol/min/mL; the catalase activity of treatment with PL-02 strain is 26 nmol/min/mL. These results demonstrate that taking CS-773 strain, TYCA06 strain, or PL-02 strain can enhance the muscle's antioxidation ability to reduce fatigue.

It is also found that the catalase activity of treatment with CS-773 strain, TYCA06 strain, and PL-02 strain (total bacterial count: $4 \times 10^8$ CFU; bacterial count ratio of all strains: 1: 1: 1) is 81 nmol/min/mL, which is greater than the sum of the catalase activity of treatment with CS-773 strain, that of treatment with TYCA06 strain, and that of treatment with PL-02 strain. These results demonstrate that taking CS-773 strain, TYCA06 strain, and PL-02 strain together can bring a synergistic effect on the muscle's antioxidation ability.

EXAMPLE 8

Anti-Absorption Test for Fatty Acid

Probiotics can degrade and utilize food to maintain the human's gastrointestinal health. Oleic acid is the most abundant fatty acid in food. Papers have reported that *Lactobacillus* could utilize palmitic acid as the material for cell membrane and then synthesize cyclopropene fatty acid so that the bacteria could resist the acidic environment in the gastrointestinal tract to increase its survival rate. As such, probiotics and intestinal cells can compete for oleic acid so as to decrease the fatty acid absorption of the intestines and the stomach. In this example, the effect of probiotics on the fatty acid absorption of intestinal cells was determined.

Human colorectal adenocarcinoma Caco-2 cells were seeded onto a culture plate in a cell density of $2 \times 10^6$ cells/well and incubated with a DMEM medium (containing 10% FBS, 1% Penicillin/Streptomycin, and 0.01 mg/mL human transferrin) for 3 days. After which, a fresh DMEM medium (containing 5% FBS) was used for substitution. After probiotics were activated for 18 hours, the strain concentration was adjusted to $2 \times 10^8$ CFU/mL with a DMEM medium (containing 2% BSA and 500 µM oleic acid). 2 mL of the bacterial liquid and 500 µM oleic acid were added to each well and incubated with the Caco-2 cells in an incubator at 37° C. for 6 hours. Finally, the Caco-2 cells were stained with oil red 0 and the intracellular fat content was analyzed according to the OD520 nm value.

Figure 11:
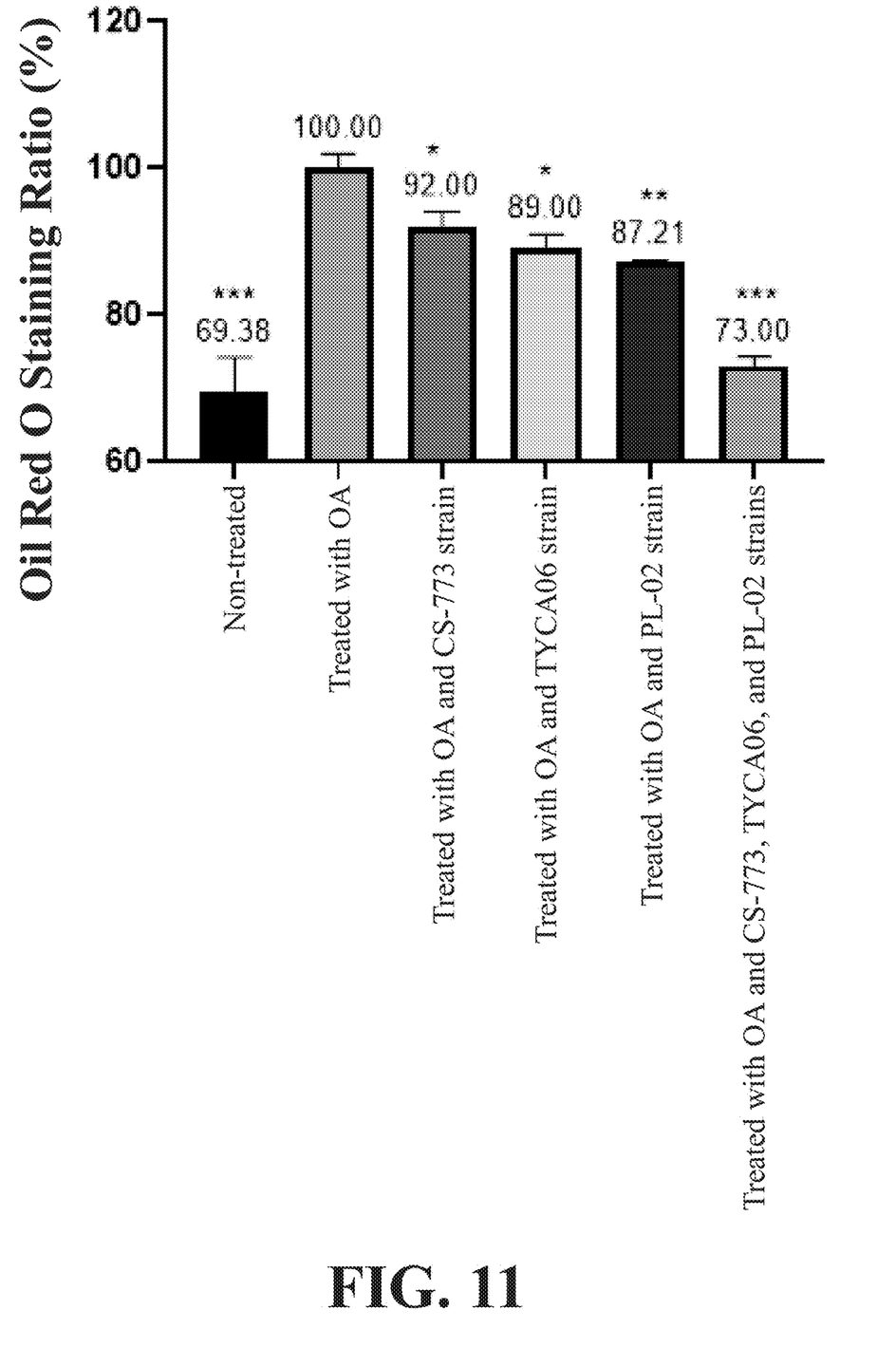
FIG. 11 is a bar graph illustrating the effect of probiotics on fatty acid absorption in human Caco-2 intestinal epithelial cells.

As shown in FIG. 11, the intracellular fat content of treatment with oleic acid is taken as 100% for normalization. Accordingly, the relative intracellular fat content of treatment with oleic acid and CS-773 strain is 92%; the relative intracellular fat content of treatment with oleic acid and TYCA06 strain is 89%; the relative intracellular fat content of treatment with oleic acid and PL-02 strain is 87.21%. These results demonstrate that CS-773 strain, TYCA06 strain, or PL-02 strain can compete with human colorectal adenocarcinoma Caco-2 cells for oleic acid so as to decrease the intracellular accumulation level of oleic acid. For these reasons, taking CS-773 strain, TYCA06 strain, or PL-02 strain can inhibit the fatty acid absorption of cells. It is further found that the relative intracellular fat content of treatment with oleic acid, CS-773 strain, TYCA06 strain, and PL-02 strain (total bacterial count: $4 \times 10^8$ CFU; bacterial count ratio of all strains: 1: 1: 1) is 73%, which demonstrates taking CS-773 strain, TYCA06 strain, and PL-02 strain together can bring a synergistic effect on the inhibition of cells' fatty acid absorption.

As above, administering CS-773 strain, TYCA06 strain, and/or PL-02 strain to human in the suggested daily dose of $2 \times 10^{10}$ CFU/day can obviously enhance muscle strength and muscle endurance. It has been found that few lactic acid bacterial strains have effect on improving body fatigue and promoting exercise performance, which has been proven in an in vivo experiment. The function of lactic acid bacteria on the human health depends on the strain specificity, not the species specificity. Additionally, the strain having special function on the human's health is called as "functional probiotics" (Joint FAO/WHO Working Group Report on Drafting Guidelines for the Evaluation of Probiotics in Food, London, Ontario, Canada, Apr. 30 and May 1, 2002).

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for reducing fat and promoting exercise performance, comprising:
   administering a lactic acid bacterial composition to a subject in need thereof;
   wherein the lactic acid bacterial composition comprises:
   a *Lactobacillus plantarum* PL-02 strain (accession number: CGMCC 20485);
   a *Lactobacillus acidophilus* TYCA06 strain (accession number: CGMCC 15210);
   a *Lactobacillus casei* CS-773 strain (accession number: CGMCC 20991); and
   a physiologically acceptable excipient, diluent, or carrier;
   wherein the PL-02 strain, the TYCA06 strain, and the CS-773 strain are deposited at the China General Microbiological Culture Collection Center.

2. The method as claimed in claim 1, wherein the composition further comprises:
   a *Bifidobacterium longum* subsp. *infantis* BLI-02 strain (accession number: CGMCC 15212); and
   a *Lactobacillus rhamnosus* bv-77 strain (accession number: CCTCC M 2014589);
   wherein the BLI-02 strain is deposited at the China General Microbiological Culture Collection Center, and the bv-77 strain is deposited at the China Center for Type Culture Collection.

3. The method as claimed in claim 1, wherein the composition further comprises:
   a *Bifidobacterium longum* subsp. infantis BLI-02 strain (accession number: CGMCC 15212); and
   a *Lactococcus lactis* LY-66 strain (accession number: CGMCC 21838);
   wherein the BLI-02 strain and the LY-66 strain are deposited at the China General Microbiological Culture Collection Center.

4. The method as claimed in claim 1, wherein the strains are administered at a daily dose per kg of human's body weight of $3.33 \times 10^8$ CFU/kg/day.

5. The method as claimed in claim 2, wherein the strains are administered at a daily dose per kg of human's body weight of $3.33 \times 10^8$ CFU/kg/day.

6. The method as claimed in claim 3, wherein the strains are administered at a daily dose per kg of human's body weight of $3.33 \times 10^8$ CFU/kg/day.

7. The method as claimed in claim 1, wherein the strains are administered at a daily dose of $2 \times 10^{10}$ CFU/day.

8. The method as claimed in claim 2, wherein the strains are administered at a daily dose of $2 \times 10^{10}$ CFU/day.

9. The method as claimed in claim 3, wherein the strains are administered at a daily dose of $2 \times 10^{10}$ CFU/day.

* * * * *